US006440706B1

(12) United States Patent
Vogelstein et al.

(10) Patent No.: US 6,440,706 B1
(45) Date of Patent: Aug. 27, 2002

(54) DIGITAL AMPLIFICATION

(75) Inventors: Bert Vogelstein, Baltimore; Kenneth W. Kinzler, BelAir, both of MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/613,826

(22) Filed: Jul. 11, 2000

Related U.S. Application Data

(60) Provisional application No. 60/146,792, filed on Aug. 2, 1999.

(51) Int. Cl.[7] .......................... C12P 19/34; C12Q 1/68; C07H 21/02; C07H 21/04; C07H 19/00
(52) U.S. Cl. .......................... 435/91.2; 435/6; 435/7.1; 435/91.1; 536/22.1; 536/23.1; 536/24.3; 536/24.31; 536/24.32; 536/24.33
(58) Field of Search .......................... 435/6, 7.1, 91.1, 435/91.2; 536/22.1, 23.1, 24.3, 24.31, 24.32, 24.33

(56) References Cited

U.S. PATENT DOCUMENTS

| | | | |
|---|---|---|---|
| 5,670,325 A | | 9/1997 | Lapidus et al. |
| 5,804,383 A | | 9/1998 | Gruenert et al. |
| 5,858,663 A | | 1/1999 | Nisson et al. |
| 5,925,517 A | * | 7/1999 | Tyagi et al. .................... 435/6 |
| 5,928,870 A | | 7/1999 | Lapidus et al. |
| 6,020,137 A | | 2/2000 | Lapidus et al. |
| 6,037,130 A | * | 3/2000 | Tyagi et al. .................... 435/6 |
| 6,143,496 A | | 11/2000 | Brown et al. |

FOREIGN PATENT DOCUMENTS

| | | |
|---|---|---|
| EP | 0643140 A | 3/1995 |
| WO | WO 95/13399 | 5/1995 |
| WO | WO 99/13113 | 3/1999 |

OTHER PUBLICATIONS

Newton Essential PCR pp. 51–52 1995.*
Darren G. Monckton, et al., "Minisatellite "Isoallele" Discrimination in Pseudohomozygotes by Single Molecule PCR and Variant Repeat Mapping", Genomics 11, pp. 465–467, 1991.
Gualberto Ruano, et al., "Haplotype of Multiple Polymorphisms Resolved by Enzymatic Amplification of Single DNA Molecules", Proc. National Science USA, 1990 vol. 87 pp 6296–6300.
W. Navidi, et al., "Using PCR in Preimplantation Genetic Disease Diagnosis", Human Reproduction, vol. 6, No. 6, pp. 836–849, 1991.
Hongua Li, et al., "Amplification and Analysis of DNA Sequences in Single Human Sperm and Diploid Cells", Nature, vol. 335, Sep. 29, 1988 pp. 414–417.
Ramon Parsons, et al., "Mismatch Repair Deficiency in Phenotypically Normal Human Cells", Science, vol. 268, May 5, 1995 pp. 738–740.

Lin Zhang, et al., "Whole Genome Amplification from a Single Cell: Implications for Genetic Analysis", Proc. National Science USA, vol. 89, pp. 5847–5851, Jul. 1992.
David Sidransky, et al., "Clonal Expansion of p53 Mutant Cells in Associated with Brain Tumor Progression", Nature, Feb. 27, 1992 vol. 355, pp. 846–847.
Alec J. Jeffreys, et al., "Mutation Processes at Human Minisatellites", Electophoresis, pp. 1577–1585, 1995.
C. Schmitt, et al., "High Sensitive DNA Typing Approaches for the Analysis of Forensic Evidence: Comparison of Nested Variable Number of Tandem Repeats (VNTR) Amplification and a Short Tandem Repeats (STR) Polymorphism", Forensic Science International, vol. 66, pp. 129–141, 1994.
Paul M. Lizardi, et al., "Mutation Detection and Single–Molecule Counting Using Isothermal Rolling–Circle Amplification", Nature Genetics, vol. 19, Jul. 1988 pp. 225–232.
A. Piatek et al., "Molecular Beacon Sequence Analysis for Detecting Drug Resistance in Mycobacterium Tuberculosis", Nature Biotechnology, Apr. 1998, pp. 359–363, vol. 16, No. 4.
S. Tyagi et al., "Multicolor Molecular Beacons for allele discrimination", Nature Biotechnology, pp. 303–308, Jan. 1998, vol. 16, No. 1.
J. A.M. Vet et al., "Multilex Detection of Four Pathogenic Retroviruses Using Molecular Beacons", Proceedings of the National Academy of Sciences of the United States, May 25, 1999, pp. 6394–6399, vol. 96, No. 11.
S. Tyagi et al., "Molecular Beacons: probes that Fluoresce Upon Hybridization", Nature Biotechnology, 1996, pp. 303–308, vol. 14, No. 3.
W. P. Halford et al., "The Inherent Quantitative Capacity of the Reverse Transcription–Polymerase Chain Reaction", Analytical Biochemistry, Jan. 15, 1999, pp. 181–191, vol. 266, No. 2.
B. Vogelstein et al., "Digital PCR", Proceedings of the National Academy of Sciences of the United States, Aug. 3, 1999, pp. 9236–9241, vol. 96, No. 16.
K. D.E. Everett et al, "Identification of nine species of the Chlamydiaceae Uisng PCR–RFLP", Apr. 1999, pp. 803–813, vol. 49, No. 2.

* cited by examiner

*Primary Examiner*—Jeffrey Siew
(74) *Attorney, Agent, or Firm*—Banner & Witcoff, Ltd.

(57) ABSTRACT

The identification of pre-defined mutations expected to be present in a minor fraction of a cell population is important for a variety of basic research and clinical applications. The exponential, analog nature of the polymerase chain reaction is transformed into a linear, digital signal suitable for this purpose. Single molecules can be isolated by dilution and individually amplified; each product is then separately analyzed for the presence of mutations. The process provides a reliable and quantitative measure of the proportion of variant sequences within a DNA sample.

64 Claims, 7 Drawing Sheets

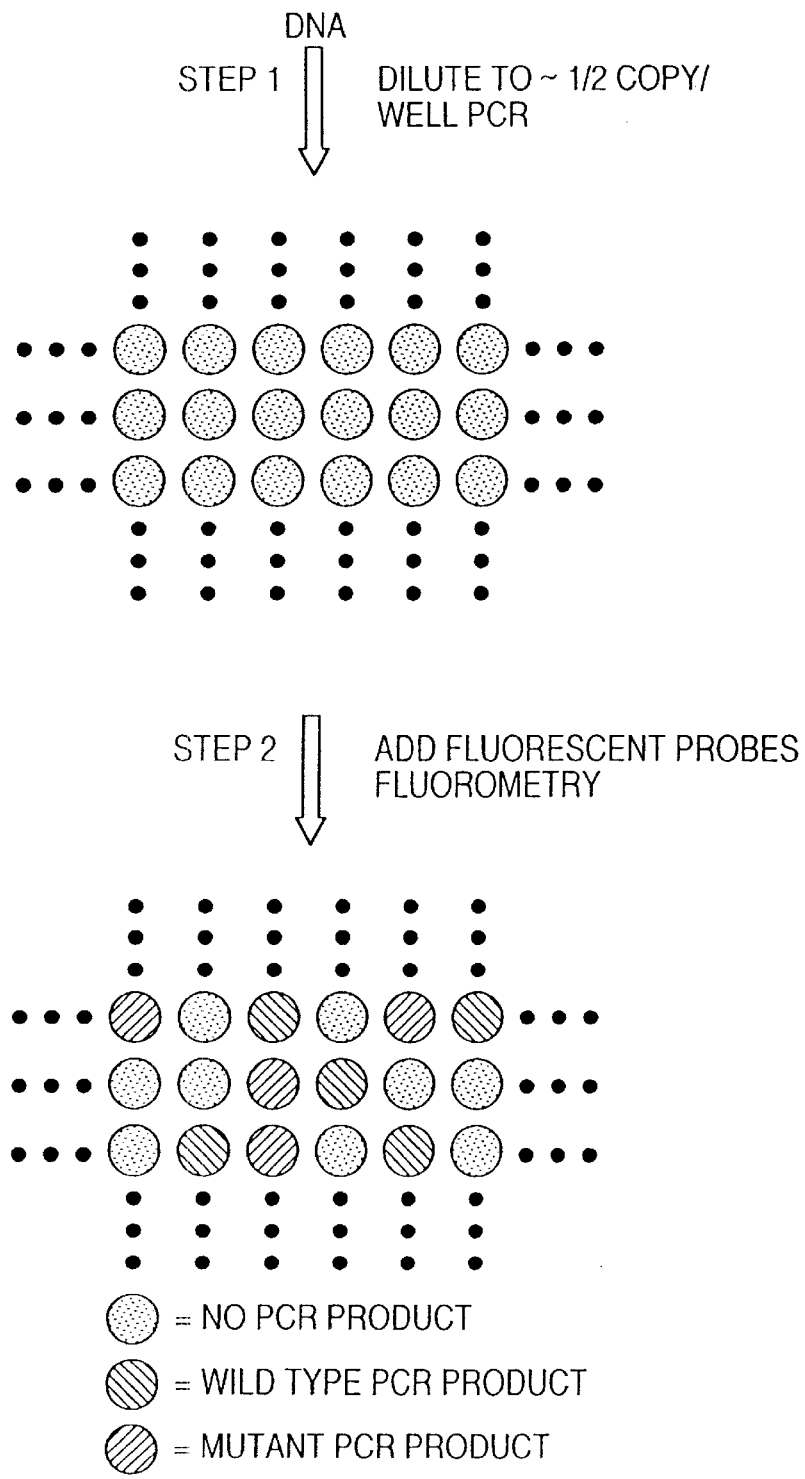

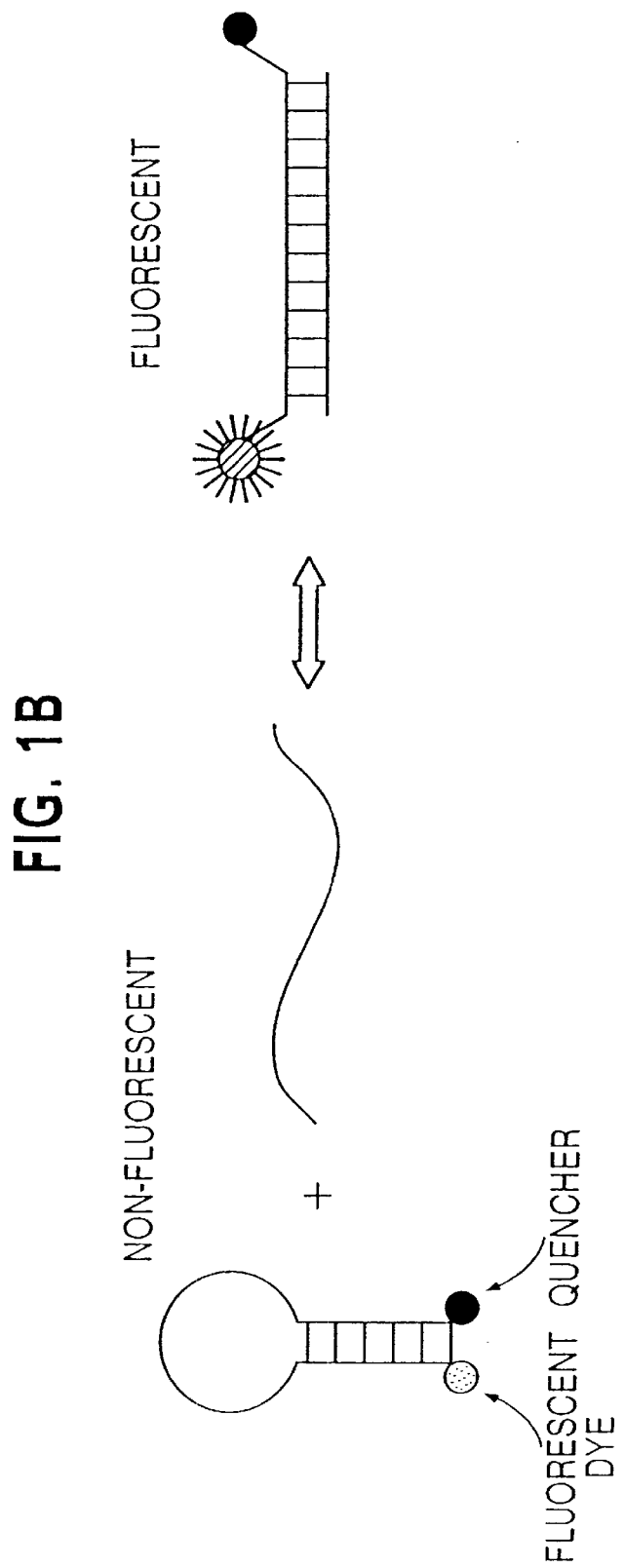

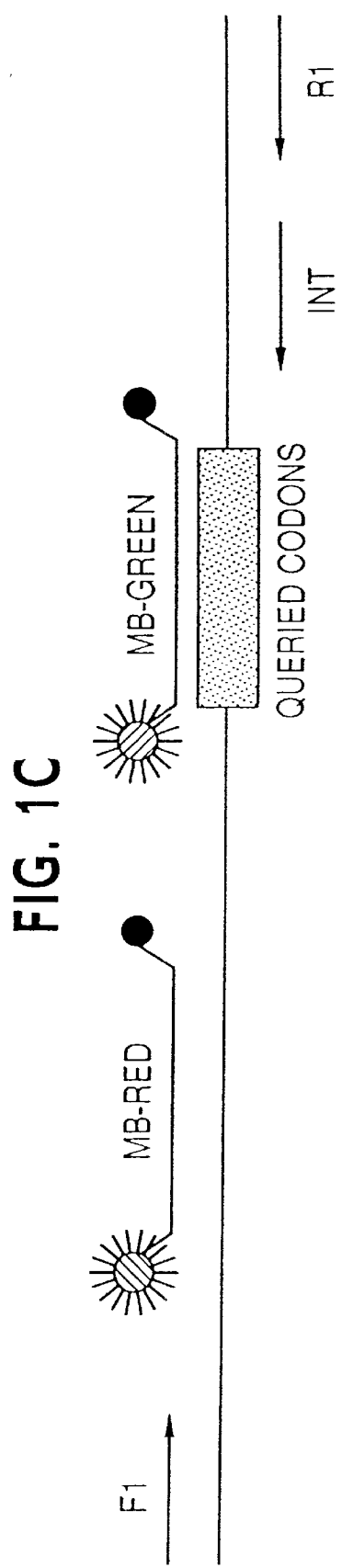

```
                            SEQUENCE LISTING

<160> NUMBER OF SEQ ID NOS: 15

<210> SEQ ID NO 1
<211> LENGTH: 26
<212> TYPE: DNA
<213> ORGANISM: homo sapiens

<400> SEQUENCE: 1
catgttctaa tatagtcaca ttttca                                          26

<210> SEQ ID NO 2
<211> LENGTH: 24
<212> TYPE: DNA
<213> ORGANISM: homo sapiens

<400> SEQUENCE: 2
tctgaattag ctgtatcgtc aagg                                            24

<210> SEQ ID NO 3
<211> LENGTH: 20
<212> TYPE: DNA
<213> ORGANISM: homo sapiens

<400> SEQUENCE: 3
tagctgtatc gtcaaggcac                                                 20

<210> SEQ ID NO 4
<211> LENGTH: 27
<212> TYPE: DNA
<213> ORGANISM: homo sapiens

<400> SEQUENCE: 4
cacgggcctg ctgaaaatga ctgcgtg                                         27

<210> SEQ ID NO 5
<211> LENGTH: 24
<212> TYPE: DNA
<213> ORGANISM: homo sapiens

<400> SEQUENCE: 5
```

-continued cacgggagct ggtggcgtag cgtg     24

<210> SEQ ID NO 6
<211> LENGTH: 24
<212> TYPE: DNA
<213> ORGANISM: homo sapiens

<400> SEQUENCE: 6
cattattttt attataaggc ctgc     24

<210> SEQ ID NO 7
<211> LENGTH: 12
<212> TYPE: DNA
<213> ORGANISM: homo sapiens

<400> SEQUENCE: 7
gctggtggcg ta     12

<210> SEQ ID NO 8
<211> LENGTH: 12
<212> TYPE: DNA
<213> ORGANISM: homo sapiens

<400> SEQUENCE: 8
gctagtggcg ta     12

<210> SEQ ID NO 9
<211> LENGTH: 12
<212> TYPE: DNA
<213> ORGANISM: homo sapiens

<400> SEQUENCE: 9
gctggtgacg ta     12

<210> SEQ ID NO 10
<211> LENGTH: 12
<212> TYPE: DNA
<213> ORGANISM: homo sapiens

<400> SEQUENCE: 10
gctcgtggcg ta     12

<210> SEQ ID NO 11
<211> LENGTH: 13
<212> TYPE: DNA
<213> ORGANISM: homo sapiens

<400> SEQUENCE: 11
gcttgtggcc gta     13

<210> SEQ ID NO 12
<211> LENGTH: 13
<212> TYPE: DNA
<213> ORGANISM: homo sapiens

<400> SEQUENCE: 12
gctgatgggc gta     13

<210> SEQ ID NO 13
<211> LENGTH: 12
<212> TYPE: DNA
<213> ORGANISM: homo sapiens

<400> SEQUENCE: 13

-continued

```
gctgatggcg ta                                                          12

<210> SEQ ID NO 14
<211> LENGTH: 12
<212> TYPE: DNA
<213> ORGANISM: homo sapiens

<400> SEQUENCE: 14
gctgctggcg ta                                                          12

<210> SEQ ID NO 15
<211> LENGTH: 12
<212> TYPE: DNA
<213> ORGANISM: homo sapiens

<400> SEQUENCE: 15
gctggtggtg ta                                                          12
```

DIGITAL AMPLIFICATION

This application claims the benefit of U.S. Ser. No. 60/146,792, filed Aug. 2, 1999.

The U.S. government retains certain rights in this invention by virtue of its support of the underlying research, supported by grants CA 43460, CA 57345, and CA 62924 from the National Institutes of Health.

TECHNICAL FIELD OF THE INVENTION

This invention is related to diagnostic genetic analyses. In particular it relates to detection of genetic changes and gene expression.

BACKGROUND OF THE INVENTION

In classical genetics, only mutations of the germ-line were considered important for understanding disease. With the realization that somatic mutations are the primary cause of cancer (1), and may also play a role in aging (2,3), new genetic principles have arisen. These discoveries have provided a wealth of new opportunities for patient management as well as for basic research into the pathogenesis of neoplasia. However, many of these opportunities hinge upon detection of a small number of mutant-containing cells among a large excess of normal cells. Examples include the detection of neoplastic cells in urine (4), stool (5,6), and sputum (7,8) of patients with cancers of the bladder, colorectum, and lung, respectively. Such detection has been shown in some cases to be possible at a stage when the primary tumors are still curable and the patients asymptomatic. Mutant sequences from the DNA of neoplastic cells have also been found in the blood of cancer patients (9–11). The detection of residual disease in lymph nodes or surgical margins may be useful in predicting which patients might benefit most from further therapy (12–14). From a basic research standpoint, analysis of the early effects of carcinogens is often dependent on the ability to detect small populations of mutant cells (15–17).

Because of the importance of this issue in so many settings, many useful techniques have been developed for the detection of mutations. DNA sequencing is the gold standard for the detection of germ line mutations, but is useful only when the fraction of mutated alleles is greater than ~20% (18,19). Mutant-specific oligonucleotides can sometimes be used to detect mutations present in a minor proportion of the cells analyzed, but the signal to noise ratio distinguishing mutant and wild-type (WT) templates is variable (20–22). The use of mutant-specific primers or the digestion of polymerase chain reaction (PCR) products with specific restriction endonucleases are extremely sensitive methods for detecting such mutations, but it is difficult to quantitate the fraction of mutant molecules in the starting population with these techniques (23–28). Other innovative approaches for the detection of somatic mutations have been reviewed (29–32). A general problem with these methods is that it is difficult or impossible to independently confirm the existence of any mutations that are identified.

Thus there is a need in the art for methods for accurately and quantitatively detecting genetic sequences in mixed populations of sequences.

SUMMARY OF THE INVENTION

It is an object of the present invention to provide methods for determining the presence of a selected genetic sequence in a population of genetic sequences.

It is another object of the present invention to provide molecular beacon probes useful in the method of the invention.

These and other objects of the invention are achieved by providing a method for determining the presence of a selected genetic sequence in a population of genetic sequences. A biological sample comprising nucleic acid template molecules is diluted to form a set of assay samples. The template molecules within the assay samples are amplified to form a population of amplified molecules in the assay samples of the set. The amplified molecules in the assay samples of the set are then analyzed to determine a first number of assay samples which contain the selected genetic sequence and a second number of assay samples which contain a reference genetic sequence. The first number is then compared to the second number to ascertain a ratio which reflects the composition of the biological sample.

Another embodiment of the invention is a method for determining the ratio of a selected genetic sequence in a population of genetic sequences. Template molecules within a set comprising a plurality of assay samples are amplified to form a population of amplified molecules in each of the assay samples of the set. The amplified molecules in the assay samples of the set are analyzed to determine a first number of assay samples which contain the selected genetic sequence and a second number of assay samples which contain a reference genetic sequence. The first number is compared to the second number to ascertain a ratio which reflects the composition of the biological sample.

According to another embodiment of the invention, a molecular beacon probe is provided. It comprises an oligonucleotide with a stem-loop structure having a photoluminescent dye at one of the 5' or 3' ends and a quenching agent at the opposite 5' or 3' end. The loop consists of 16 base pairs and has a $T_m$ of 50–51° C. The stem consists of 4 base pairs having a sequence 5'-CACG-3'.

A second type of molecular beacon probe is provided in another embodiment. It comprises an oligonucleotide with a stem-loop structure having a photoluminescent dye at one of the 5' or 3' ends and a quenching agent at the opposite 5' or 3' end. The loop consists of 19–20 base pairs and has a $T_m$ of 54–56° C. The stem consists of 4 base pairs having a sequence 5'-CACG-3'.

Another embodiment provides the two types of molecular beacon probes, either mixed together or provided in a divided container as a kit.

The invention thus provides the art with the means to obtain quantitative assessments of particular DNA or RNA sequences in mixed populations of sequences using digital (binary) signals.

BRIEF DESCRIPTION OF THE DRAWINGS

FIGS. 1A, 1B, 1C. Schematic of experimental design. (A) The basic two steps involved: PCR on diluted DNA samples is followed by addition of fluorescent probes which discriminate between WT and mutant alleles and subsequent fluorometry. (B) Principle of molecular beacon analysis. In the stem-loop configuration, fluorescence from a dye at the 5' end of the oligonucleotide probe is quenched by a Dabcyl group at the 3' end. Upon hybridization to a template, the dye is separated from the quencher, resulting in increased fluorescence. Modified from Marras et al. (C) Oligonucleotide design. Primers F1 and R1 are used to amplify the genomic region of interest. Primer INT is used to produce single stranded DNA from the original PCR products during a subsequent asymmetric PCR step (see Materials and Methods). MB-RED is a Molecular Beacon which detects any appropriate PCR product, whether it is WT or mutant at the queried codons. MB-GREEN is a Molecular Beacon which preferentially detects the WT PCR product.

DETAILED DESCRIPTION OF THE INVENTION

Figure 2:
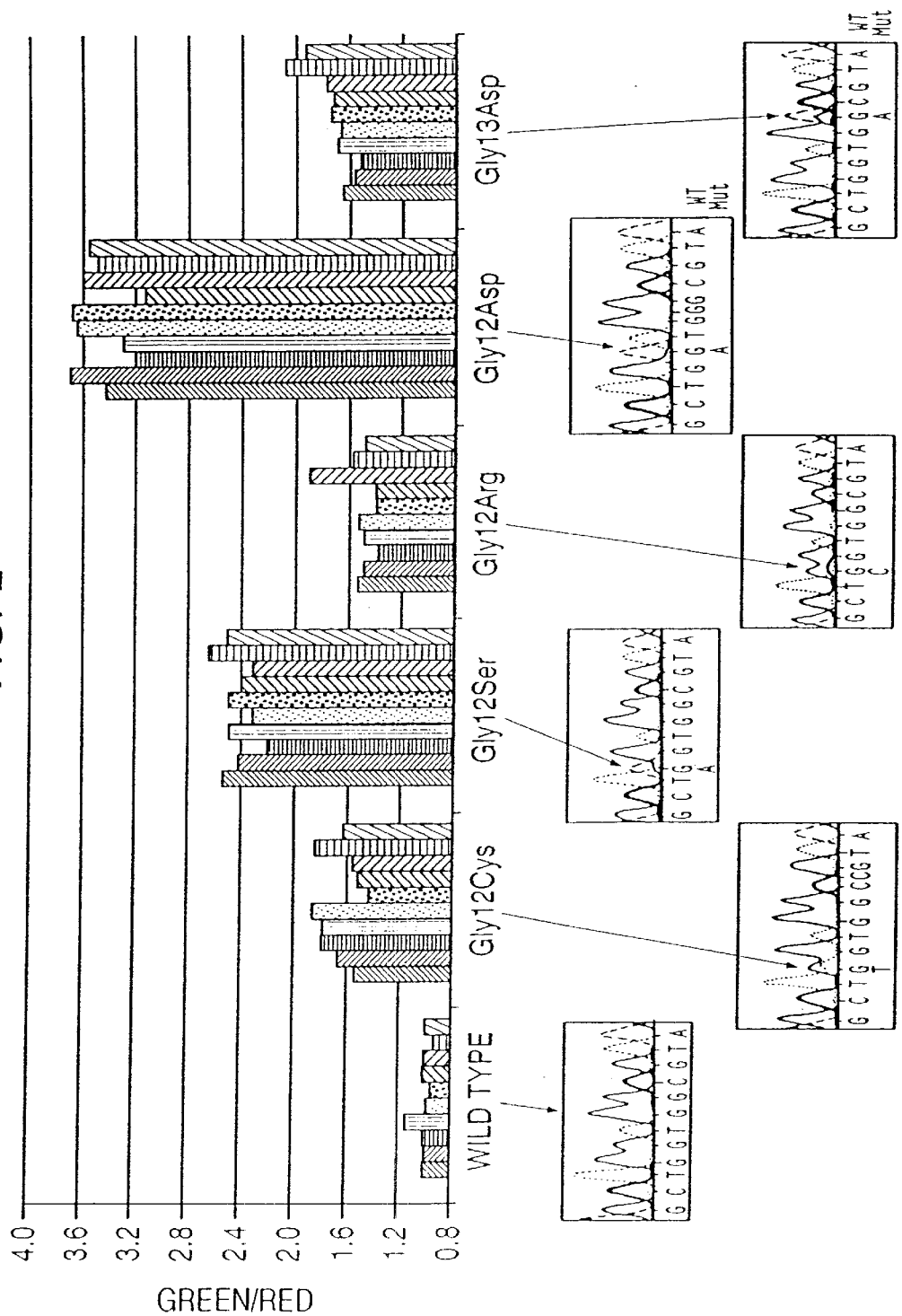
FIG. 2. Discrimination between WT and mutant PCR products by Molecular Beacons. Ten separate PCR products, each generated from ~25 genome equivalents of genomic DNA of cells containing the indicated mutations of c-Ki-Ras, were analyzed with the Molecular Beacon probes described in the text. Representative examples of the PCR products used for Molecular Beacon analysis were purified and directly sequenced. In the cases with Gly12Cys (SEQ ID NO: 11) and Gly12Arg (SEQ ID NO: 10) mutations, contaminating non-neoplastic cells within the tumor presumably accounted for the relatively low ratios. In the cases with Gly12Ser (SEQ ID NO: 8) and Gly12Asp (SEQ ID NO: 12), there were apparently two or more alleles of mutant c-Ki-Ras for every WT allele (SEQ ID NO: 7); both these tumors were aneuploid. Analysis of the Gly13Asp mutation is also shown (SEQ ID NO: 9).

The method devised by the present inventors involves separately amplifying small numbers of template molecules so that the resultant products have a proportion of the analyte sequence which is detectable by the detection means chosen. At its limit, single template molecules can be amplified so that the products are completely mutant or completely wild-type (WT). The homogeneity of these amplification products makes them trivial to distinguish through existing techniques.

The method requires analyzing a large number of amplified products simply and reliably. Techniques for such assessments were developed, with the output providing a digital readout of the fraction of mutant alleles in the analyzed population.

The biological sample is diluted to a point at which a practically usable number of the diluted samples contain a proportion of the selected genetic sequence (analyte) relative to total template molecules such that the analyzing technique being used can detect the analyte. A practically usable number of diluted samples will depend on cost of the analysis method. Typically it would be desirable that at least 1/50 of the diluted samples have a detectable proportion of analyte. At least 1/10, 1/5, 3/10, 2/5, 1/2, 3/5, 7/10, 4/5, or 9/10 of the diluted samples may have a detectable proportion of analyte. The higher the fraction of samples which will provide useful information, the more economical will be the overall assay. Over-dilution will also lead to a loss of economy, as many samples will be analyzed and provide no signal. A particularly preferred degree of dilution is to a point where each of the assay samples has on average one-half of a template. The dilution can be performed from more concentrated samples. Alternatively, dilute sources of template nucleic acids can be used. All of the samples may contain amplifiable template molecules. Desirably each assay sample prior to amplification will contain less than a hundred or less than ten template molecules.

Digital amplification can be used to detect mutations present at relatively low levels in the samples to be analyzed. The limit of detection is defined by the number of wells that can be analyzed and the intrinsic mutation rate of the polymerase used for amplification. 384 well PCR plates are commercially available and 1536 well plates are on the horizon, theoretically allowing sensitivities for mutation detection at the ~0.1% level. It is also possible that Digital Amplification can be performed in microarray format, potentially increasing the sensitivity by another order of magnitude. This sensitivity may ultimately be limited by polymerase errors. The effective error rate in PCR as performed under our conditions was <0.3%, i.e., in control experiments with DNA from normal cells, none of 340 wells containing PCR products exhibited RED/GREEN ratios >3.0. Any individual mutation (such as a G- to C-transversion at the second position of codon 12 of c-Ki-ras) is expected to occur in <1 in 50 polymerase-generated mutants (there are at least 50 base substitutions within or surrounding codons 12 and 13 that should yield high RED/GREEN ratios). Determining the sequence of the putative mutants in the positive wells, by direct sequencing as performed here or by any of the other techniques, provides unequivocal validation of a prospective mutation: a significant fraction of the mutations found in individual wells should be identical if the mutation occurred in vivo. Significance can be established through rigorous statistical analysis, as positive signals should be distributed according to Poisson probabilities. Moreover, the error rate in particular Digital Amplification experiments can be precisely determined through performance of Digital Amplification on DNA templates from normal cells.

Digital Amplification is as easily applied to RT-PCR products generated from RNA templates as it is to genomic DNA. For example, the fraction of alternatively spliced or mutant transcripts from a gene can be easily determined using photoluminescent probes specific for each of the PCR products generated. Similarly, Digital Amplification can be used to quantitate relative levels of gene expression within an RNA population. For this amplification, each well would contain primers which are used to amplify a reference transcript expressed constitutively as well as primers specific for the experimental transcript. One photoluminescent probe would then be used to detect PCR products from the reference transcript and a second photoluminescent probe used for the test transcript. The number of wells in which the test transcript is amplified divided by the number of wells in which the reference transcript is amplified provides a quantitative measure of gene expression. Another group of examples involves the investigations of allelic status when two mutations are observed upon sequence analysis of a standard DNA sample. To distinguish whether one variant is present in each allele (vs. both occurring in one allele), cloning of PCR products is generally performed. The approach described here would simplify the analysis by eliminating the need for cloning. Other potential applications of Digital Amplification are listed in Table 1. When the goal is the quantitation of the proportion of two relatively common alleles or transcripts rather than the detection of rare alleles, techniques such as those employing TaqMan and real time PCR provide an excellent alternative to use of molecular beacons. Advantages of real time PCR methods include their simplicity and the ability to analyze multiple samples simultaneously. However, Digital Amplification may prove useful for these applications when the expected differences are small, (e.g., only ~2-fold, such as occurs with allelic imbalances (55)).

The ultimate utility of Digital Amplification lies in its ability to convert the intrinsically exponential nature of PCR to a linear one. It should thereby prove useful for experiments requiring the investigation of individual alleles, rare variants/mutations, or quantitative analysis of PCR products.

In one preferred embodiment each diluted sample has on average one half a template molecule. This is the same as one half of the diluted samples having one template molecule. This can be empirically determined by amplification. Either the analyte (selected genetic sequence) or the reference genetic sequence can be used for this determination. If the analysis method being used can detect analyte when present at a level of 20%, then one must dilute such that a significant number of diluted assay samples contain more than 20% of analyte. If the analysis method being used requires 100% analyte to detect, then dilution down to the single template molecule level will be required.

To achieve a dilution to approximately a single template molecule level, one can dilute such that between 0.1 and 0.9 of the assay samples yield an amplification product. More preferably the dilution will be to between 0.1 and 0.6, more preferably to between 0.3 and 0.5 of the assay samples yielding an amplification product.

The digital amplification method requires analysis of a large number of samples to get meaningful results. Preferably at least ten diluted assay samples are amplified and analyzed. More preferably at least 15, 20, 25, 30, 40, 50, 75, 100, 500, or 1000 diluted assay samples are amplified and analyzed. As in any method, the accuracy of the determination will improve as the number of samples increases, up to a point. Because a large number of samples must be analyzed, it is desirable to reduce the manipulative steps, especially sample transfer steps. Thus it is preferred that the steps of amplifying and analyzing are performed in the same receptacle. This makes the method an in situ, or "one-pot" method.

The number of different situations in which the digital amplification method will find application is large. Some of these are listed in Table 1. As shown in the examples, the method can be used to find a tumor mutation in a population of cells which is not purely tumor cells. As described in the examples, a probe for a particular mutation need not be used, but diminution in binding to a wild-type probe can be used as an indicator of the presence of one or more mutations. Chromosomal translocations which are characteristic of leukemias or lymphomas can be detected as a measure of the efficacy of therapy. Gene amplifications are characteristic of certain disease states. These can be measured using digital amplification. Alternatively spliced forms of a transcript can be detected and quantitated relative to other forms of the transcript using digital amplification on cDNA made from mRNA. Similarly, using cDNA made from mRNA one can determine relative levels of transcription of two different genes. One can use digital amplification to distinguish between a situation where one allele carries two mutations and one mutation is carried on each of two alleles in an individual. Allelic imbalances often result from a disease state. These can be detected using digital amplification.

Biological samples which can be used as the starting material for the analyses may be from any tissue or body sample from which DNA or mRNA can be isolated. Preferred sources include stool, blood, and lymph nodes. Preferably the biological sample is a cell-free lysate.

TABLE 1

Potential Applications of Dig-PCR

| Application | Example | Probe 1 Detects: | Probe 2 Detects: |
|---|---|---|---|
| Base substitution mutations | Cancer gene mutations in stool, blood, lymph nodes | mutant or WT alleles | WT PCR products |
| Chromosomal translocations | Residual leukemia cells after therapy (DNA or RNA) | normal or translocated alleles | translocated allele |
| Gene amplifications | Determine presence or extent of amplification | sequence within amplicon | sequence from another part of same chromosome arm |
| Alternatively spliced products | Determine fraction of alternatively spliced transcripts from same gene (RNA) | minor exons | ccomon exons |
| Changes in gene expression | Determine relative levels of expression of two genes (RNA) | first transcript | reference transcript |
| Allelic discrimination | Two different alleles mutated vs. one mutation in each of two alleles | first mutation | second mutation |

TABLE 1-continued

Potential Applications of Dig-PCR

| Application | Example | Probe 1 Detects: | Probe 2 Detects: |
| --- | --- | --- | --- |
| Allelic imbalance | Quantitative analysis with non-polymorphic markers | marker from test chromosome | marker from reference chromosome |

Molecular beacon probes according to the present invention can utilize any photoluminescent moiety as a detectable moiety. Typically these are dyes. Often these are fluorescent dyes. Photoluminescence is any process in which a material is excited by radiation such as light, is raised to an excited electronic or vibronic state, and subsequently re-emits that excitation energy as a photon of light. Such processes include fluorescence, which denotes emission accompanying descent from an excited state with paired electrons (a "singlet" state) or unpaired electrons (a "triplet" state) to a lower state with the same multiplicity, i.e., a quantum-mechanically "allowed" transition. Photoluminescence also includes phosphorescence which denotes emission accompanying descent from an excited triplet or singlet state to a lower state of different multiplicity, i.e., a quantum mechanically "forbidden" transition. Compared to "allowed" transitions, "forbidden" transitions are associated with relatively longer excited state lifetimes.

The quenching of photoluminescence may be analyzed by a variety of methods which vary primarily in terms of signal transduction. Quenching may be transduced as changes in the intensity of photoluminescence or as changes in the ratio of photoluminescence intensities at two different wavelengths, or as changes in photoluminescence lifetimes, or even as changes in the polarization (anisotropy) of photoluminescence. Skilled practitioners will recognize that instrumentation for the measurement of these varied photoluminescent responses are known. The particular ratiometric methods for the analysis of quenching in the instant examples should not be construed as limiting the invention to any particular form of signal transduction. Ratiometric measurements of photoluminescence intensity can include the measurement of changes in intensity, photoluminescence lifetimes, or even polarization (anisotropy).

Although the working examples demonstrate the use of molecular beacon probes as the means of analysis of the amplified dilution samples, other techniques can be used as well. These include sequencing, gel TaqMan™ (dual-labeled fluorogenic) probes (Perkin Elmer Corp./Applied Biosystems, Foster City, Calif.), pyrene-labeled probes, and other biochemical assays.

The above disclosure generally describes the present invention. A more complete understanding can be obtained by reference to the following specific examples which are provided herein for purposes of illustration only, and are not intended to limit the scope of the invention.

EXAMPLE 1

Step 1: PCR amplifications. The optimal conditions for PCR described in this section were determined by varying the parameters described in the Results. PCR was performed in 7 ul volumes in 96 well polypropylene PCR plates (Marsh Biomedical Products, Rochester, N.Y.). The composition of the reactions was: 67 mM Tris, pH 8.8, 16.6 mM $NH_4SO_4$, 6.7 mM $MgCl_2$, 10 mM β-mercaptoethanol, 1 mM dATP, 1 mM dCTP, 1 mM dGTP, 1 mM TTP, 6% DMSO, 1 uM primer F1, 1 uM primer R1, 0.05 units/ul Platinum Taq polymerase (Life Technologies, Inc.), and "one-half genome equivalent" of DNA. To determine the amount of DNA corresponding to one-half genome equivalent, DNA samples were serially diluted and tested via PCR. The amount that yielded amplification products in half the wells, usually ~1.5 pg of total DNA, was defined as "one-half genome equivalent" and used in each well of subsequent Digital Amplification experiments. Fifty ul light mineral oil (Sigma M-3516) was added to each well and reactions performed in a HybAid Thermal cycler at the following temperatures: denaturation at 94° for one min; 60 cycles of 94° for 15 sec, 55° for 15 sec., 70° for 15 seconds; 70° for five minutes. Reactions were read immediately or stored at room temperature for up to 36 hours before fluorescence analysis.

EXAMPLE 2

Step 2: Fluorescence analysis. 3.5 ul of a solution with the following composition was added to each well: 67 mM Tris, pH 8.8, 16.6 mM $NH_4SO_4$, 6.7 mM $MgCl_2$, 10 mM β-mercaptoethanol, 1 mM dATP, 1 mM dCTP, 1 mM dGTP, 1 mM TTP, 6% DMSO, 5 uM primer INT, 1 uM MB-GREEN, 1 uM MB-RED, 0.1 units/ul Platinum Taq polymerase. The plates were centrifuged for 20 seconds at 6000 g and fluorescence read at excitation/emission wavelengths of 485 nm/530 nm for MB-GREEN and 530 nm/590 nm for MB-RED. The fluorescence in wells without template was typically 10,000 to 20,000 fluorescence "units", with about 75% emanating from the fluorometer background and the remainder from the MB probes. The plates were then placed in a thermal cycler for asymmetric amplification at the following temperatures: 94° for one minute; 10–15 cycles of 94° for 15 sec, 55° for 15 sec., 70° for 15 seconds; 94° for one minute; and 60° for five minutes. The plates were then incubated at room temperature for ten to sixty minutes and fluorescence measured as described above. Specific fluorescence was defined as the difference in fluorescence before and after the asymmetric amplification. RED/GREEN ratios were defined as the specific fluorescence of MB-RED divided by that of MB-GREEN. RED/GREEN ratios were normalized to the ratio exhibited by the positive controls (25 genome equivalents of DNA from normal cells, as defined above in Example 1). We found that the ability of MB probes to discriminate between WT and mutant sequences under our conditions could not be reliably determined from experiments in which they were tested by hybridization to relatively short complementary single stranded oligonucleotides, and that actual PCR products had to be used for validation.

EXAMPLE 3

Oligonucleotides and DNA sequencing. Primer F1:
5'-CATGTTCTAATATAGTCACATTTTCA-3' (SEQ ID NO: 1); Primer R1:
5'-TCTGAATTAGCTGTATCGTCAAGG-3' (SEQ ID NO: 2); Primer INT:

5'-TAGCTGTATCGTCAAGGCAC-3' (SEQ ID NO: 3); MB-RED:

5'-Cy3-CACGGGCCTGCTGAAAATGACTGCGTG-Dabcyl-3' (SEQ ID NO: 4);

MB-GREEN: 5'-Fluorescein-CACGGGAGCTGGTGGCGTAGCGTG-Dabcyl-3' (SEQ ID NO: 5). Molecular Beacons (33,34) were synthesized by Midland Scientific and other oligonucleotides were synthesized by Gene Link (Thornwood, N.Y.). All were dissolved at 50 uM in TE (10 mM Tris, pH 8.0/1 mM EDTA) and kept frozen and in the dark until use. PCR products were purified using QIAquick PCR purification kits (Qiagen). In the relevant experiments described in the text, 20% of the product from single wells was used for gel electrophoresis and 40% was used for each sequencing reaction. The primer used for sequencing was 5'-CATTATTTTTATTATAAGGCCTGC-3' (SEQ ID NO: 6). Sequencing was performed using fluorescently-labeled ABI Big Dye terminators and an ABI 377 automated sequencer.

EXAMPLE 4

Principles underlying experiment. The experiment is outlined in FIG. 1A. First, the DNA is diluted into multiwell plates so that there is, on average, one template molecule per two wells, and PCR is performed. Second, the individual wells are analyzed for the presence of PCR products of mutant and WT sequence using fluorescent probes.

As the PCR products resulting from the amplification of single template molecules should be homogeneous in sequence, a variety of standard techniques could be used to assess their presence. Fluorescent probe-based technologies, which can be performed on the PCR products "in situ" (i.e., in the same wells) are particularly well-suited for this application (31, 33–40). We chose to explore the utility of one such technology, involving Molecular Beacons (MB), for this purpose (33,34). MB probes are oligonucleotides with stem-loop structures that contain a fluorescent dye at the 5' end and a quenching agent (Dabcyl) at the 3' end (FIG. 1B). The degree of quenching via fluorescence energy resonance transfer is inversely proportional to the $6^{th}$ power of the distance between the Dabcyl group and the fluorescent dye. After heating and cooling, MB probes reform a stem-loop structure which quenches the fluorescent signal from the dye (41). If a PCR product whose sequence is complementary to the loop sequence is present during the heating/cooling cycle, hybridization of the MB to one strand of the PCR product will increase the distance between the Dabcyl and the dye, resulting in increased fluorescence.

A schematic of the oligonucleotides used for Digital Amplifications shown in FIG. 1C. Two unmodified oligonucleotides are used as primers for the PCR reaction. Two MB probes, each labeled with a different fluorophore, are used to detect the PCR products. MB-GREEN has a loop region that is complementary to the portion of the WT PCR product that is queried for mutations. Mutations within the corresponding sequence of the PCR product should significantly impede its hybridization to the MB probe (33,34). MB-RED has a loop region that is complementary to a different portion of the PCR product, one not expected to be mutant. It thus should produce a signal whenever a well contains a PCR product, whether that product is WT or mutant in the region queried by MB-GREEN. Both MB probes are used together to simultaneously detect the presence of a PCR product and its mutational status.

Practical Considerations. Numerous conditions were optimized to define conditions that could be reproducibly and generally applied. As outlined in FIG. 1A, the first step involves amplification from single template molecules. Most protocols for amplification from small numbers of template molecules use a nesting procedure, wherein a product resulting from one set of primers is used as template in a second reaction employing internal primers. As many applications of digital amplification are expected to require hundreds or thousands of separate amplifications, such nesting would be inconvenient and could lead to contamination problems. Hence, conditions were sought that would achieve robust amplification without nesting. The most important of these conditions involved the use of a polymerase that was activated only after heating (44,45) and optimized concentrations of dNTP's, primers, buffer components, and temperature. The conditions specified in Examples 1–3 were defined after individually optimizing each of these components and proved suitable for amplification of several different human genomic DNA sequences. Though the time required for PCR was not particularly long (~2.5 hr), the number of cycles used was high and excessive compared to the number of cycles required to amplify the "average" single template molecule. The large cycle number was necessary because the template in some wells might not begin to be amplified until several PCR cycles had been completed. The large number of cycles ensured that every well (not simply the average well) would generate a substantial and roughly equal amount of PCR product if a template molecule were present within it.

The second step in FIG. 1A involves the detection of these PCR products. It was necessary to considerably modify the standard MB probe approach in order for it to function efficiently in Digital Amplification applications. Theoretically, one separate MB probe could be used to detect each specific mutation that might occur within the queried sequence. By inclusion of one MB corresponding to WT sequence and another corresponding to mutant sequence, the nature of the PCR product would be revealed. Though this strategy could obviously be used effectively in some situations, it becomes complex when several different mutations are expected to occur within the same queried sequence. For example, in the c-Ki-Ras gene example explored here, twelve different base substitutions resulting in missense mutations could theoretically occur within codons 12 and 13, and at least seven of these are observed in naturally-occurring human cancers. To detect all twelve mutations as well as the WT sequence with individual Molecular Beacons would require 13 different probes. Inclusion of such a large number of MB probes would raise the background fluorescence and cost of the assay. We therefore attempted to develop a single probe that would react with WT sequences better than any mutant sequence within the queried sequence. We found that the length of the loop sequence, its melting temperature, and the length and sequence of the stem were each important in determining the efficacy of such probes. Loops ranging from 14 to 26 bases and stems ranging from 4 to 6 bases, as well as numerous sequence variations of both stems and loops, were tested during the optimization procedure. For discrimination between WT and mutant sequences (MB-GREEN probe), we found that a 16 base pair loop, of melting temperature (Tm) 50–51°, and a 4 bp stem, of sequence 5'-CACG-3', were optimal. For MB-RED probes, the same stem, with a 19–20 bp loop of Tm 54–56°, proved optimal. The differences in the loop sizes and melting temperatures between MB-GREEN and MB-RED probes reflected the fact that only the GREEN probe is designed to discriminate between closely related sequences, with a shorter region of homology facilitating such discrimination.

Examples of the ratios obtained in replicate wells containing DNA templates from colorectal tumor cells with mutations of c-Ki-Ras are shown in FIG. 2. In this experiment, fifty genome equivalents of DNA were added to each well prior to amplification. Each of six tested mutants yielded ratios of RED/GREEN fluorescence that were significantly in excess of the ratio obtained with DNA from normal cells (1.5 to 3.4 in the mutants compared to 1.0 in normal DNA; p <0.0001 in each case, Student's t-Test). The reproducibility of the ratios can be observed in this figure. Direct DNA sequencing of the PCR products used for fluorescence analysis showed that the RED/GREEN ratios were dependent on the relative fraction of mutant genes within the template population (FIG. 2). Thus, the DNA from cells containing one mutant c-Ki-Ras allele per every two WT c-Ki-Ras allele yielded a RED/GREEN ratio of 1.5 (Gly12Arg mutation) while the cells containing three mutant c-Ki-Ras alleles per WT allele exhibited a ratio of 3.4 (Gly12Asp). These data suggested that wells containing only mutant alleles (no WT) would yield ratios in excess of 3.0, with the exact value dependent on the specific mutation.

Though this mode is the most convenient for many applications, we found it useful to add the MB probes after the PCR-amplification was complete (FIG. 1). This allowed us to use a standard multiwell plate fluorometer to sequentially analyze a large number of multiwell plates containing pre-formed PCR products and bypassed the requirement for multiple real time PCR instruments. Additionally, we found that the fluorescent signals obtained could be considerably enhanced if several cycles of asymmetric, linear amplification were performed in the presence of the MB probes. Asymmetric amplification was achieved by including an excess of a single internal primer (primer INT in FIG. 1C) at the time of addition of the MB probes.

EXAMPLE 5

Figure 3:
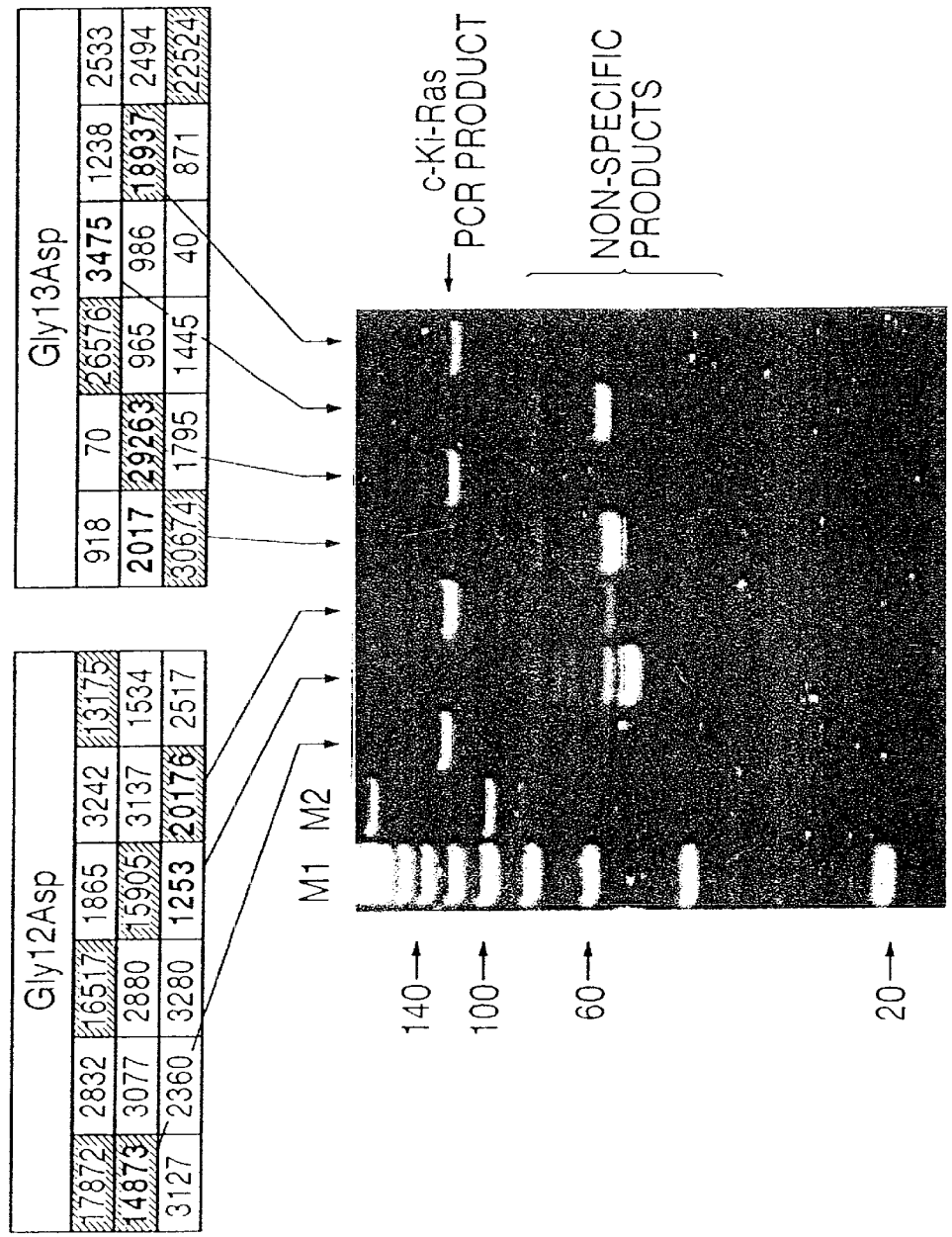
FIG. 3. Detecting Dig-PCR products with MB-RED. Specific Fluorescence Units of representative wells from an experiment employing colorectal cancer cells with Gly12Asp or Gly13Asp mutations of the c-Ki-Ras gene. Wells with values >10,000 are shaded yellow. Polyacrylamide gel electrophoretic analyses of the PCR products from selected wells are shown. Wells with fluorescence values <3500 had no PCR product of the correct size while wells with fluorescence values >10,000 SFU always contained PCR products of 129 bp. Non-specific products generated during the large number of cycles required for Dig-PCR did not affect the fluorescence analysis. M1 and M2 are molecular weight markers used to determine the size of fragments indicated on the left (in base pairs).
Figure 4:
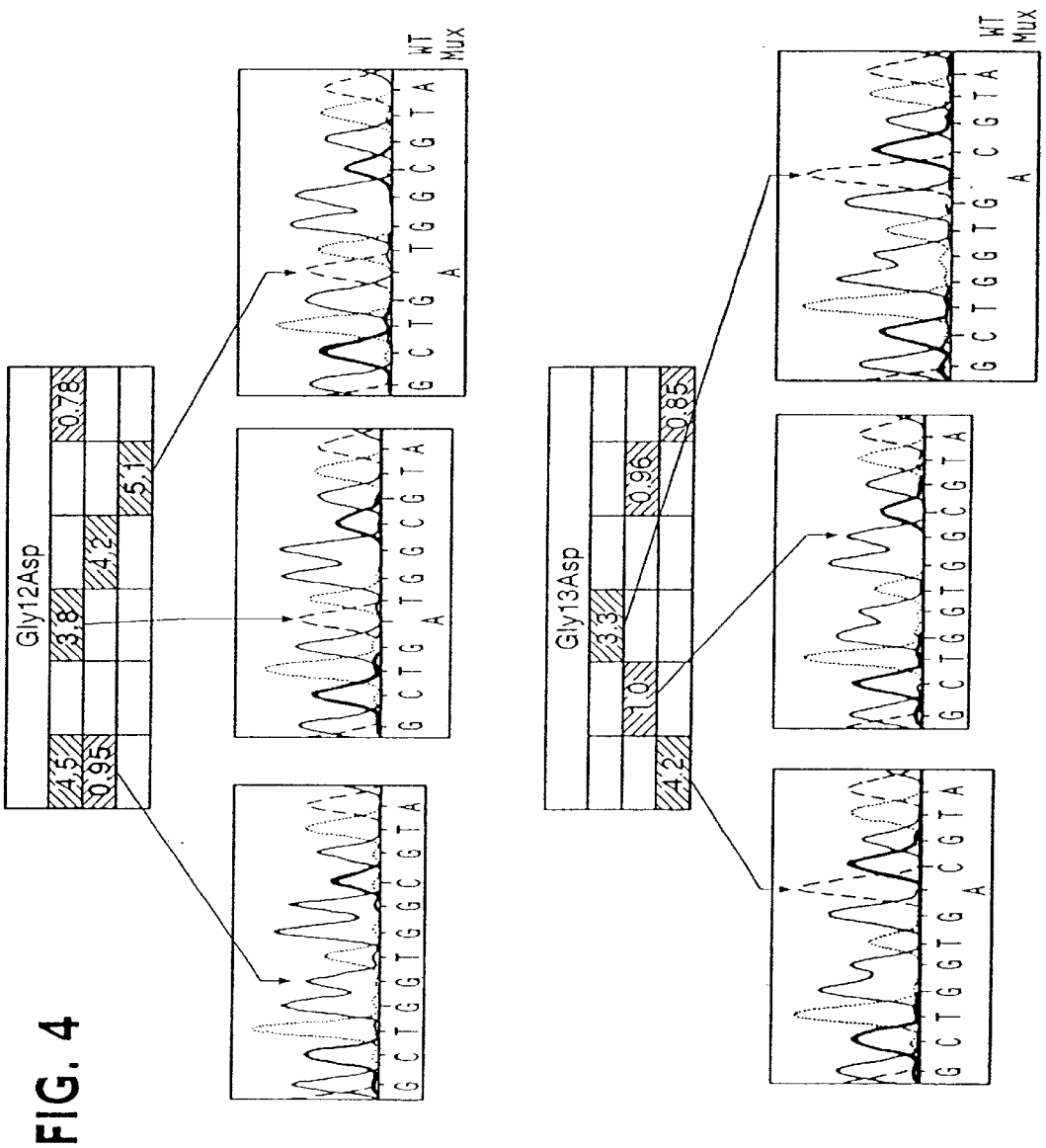
FIG. 4. Discriminating WT from mutant PCR products obtained in Dig-PCR. RED/GREEN ratios were determined from the fluorescence of MB-RED and MB-GREEN as described in Materials and Methods. The wells shown are the same as those illustrated in FIG. 3. The sequences of PCR products from the indicated wells were determined as described in Materials and Methods. The wells with RED/GREEN ratios >3.0 each contained mutant sequences while those with RED/GREEN ratios of ~1.0 contained WT sequences. WT c-Ki-Ras (SEQ ID NO: 7), Gly12Asp (SEQ ID NO: 13), and Gly13Asp (SEQ ID NO: 9) were analyzed.

Analysis of DNA from tumor cells. The principles and practical considerations described above were illustrated with DNA from two colorectal cancer cell lines, one with a mutation in c-Ki-Ras codon 12 and the other in codon 13. Representative examples of the MB-RED fluorescence values obtained are shown in FIG. 3. There was a clear biphasic distribution, with "positive" wells yielding values in excess of 10,000 specific fluorescence units (SFU, as defined in Materials and Methods) and "negative" wells yielding values less than 3500 SFU. Gel electrophoreses of 127 such wells demonstrated that all positive wells, but no negative wells, contained PCR products of the expected size (FIG. 3). The RED/GREEN fluorescence ratios of the positive wells are shown in FIG. 4. Again, a biphasic distribution was observed. In the experiment with the tumor containing a Gly12Asp mutation, 64% of the positive wells exhibited RED/GREEN ratios in excess of 3.0 while the other 36% of the positive wells exhibited ratios ranging from 0.8 to 1.1. In the case of the tumor with the Gly13Asp mutation, 54% of the positive wells exhibited RED/GREEN ratios >3.0 while the other positive wells yielded ratios ranging from 0.9 to 1.1. The PCR products from 16 positive wells were used as sequencing templates (FIG. 4). All the wells yielding a ratio in excess of 3.0 were found to contain mutant c-Ki-Ras fragments of the expected sequence, while WT sequence was found in the other PCR products. The presence of homogeneous WT or mutant sequence confirmed that the amplification products were usually derived from single template molecules. The ratios of WT to mutant PCR products determined from the Digital Amplification assay was also consistent with the fraction of mutant alleles inferred from direct sequence analysis of genomic DNA from the two tumor lines (FIG. 2).

Figure 5:
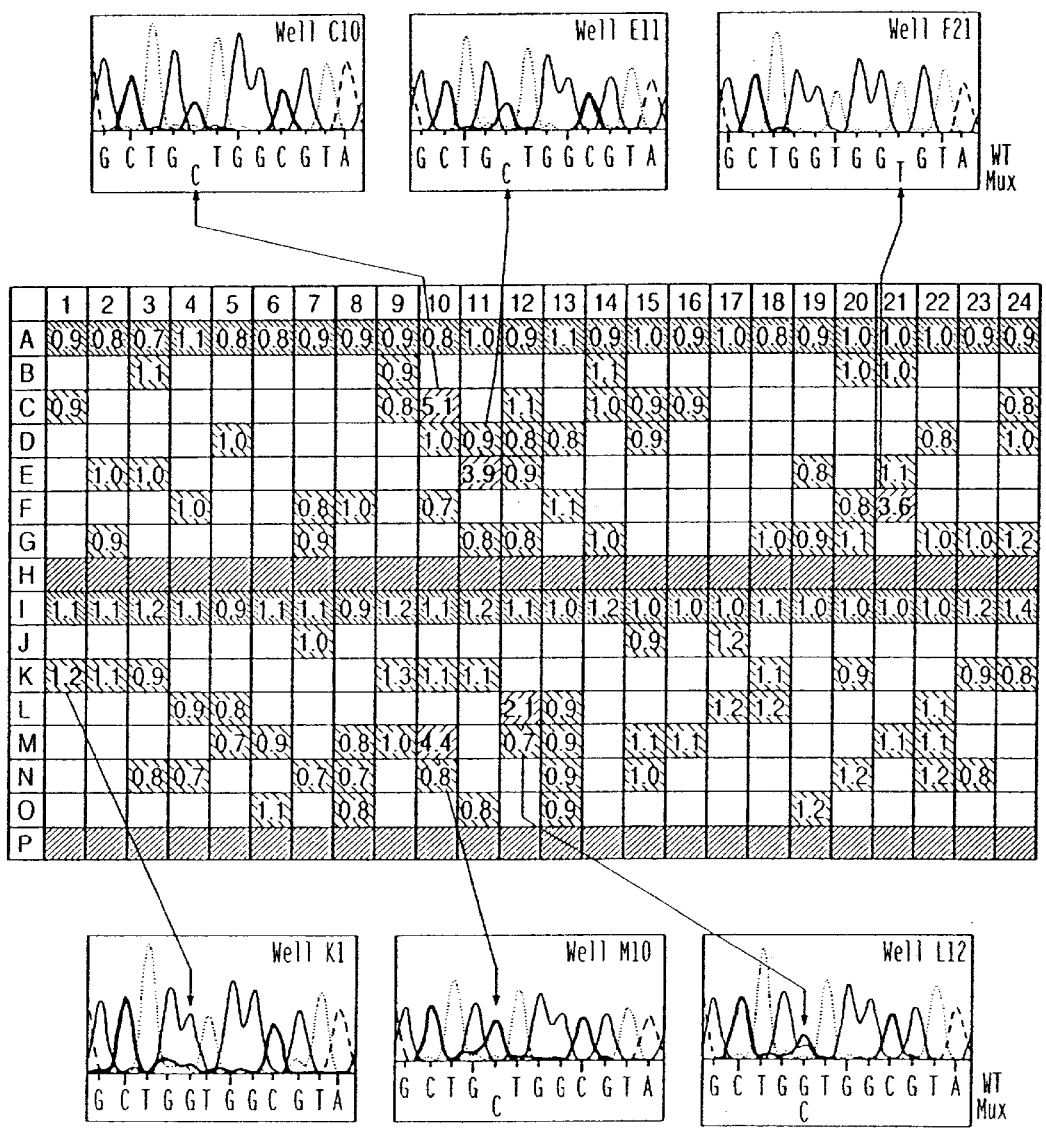
FIG. 5. Dig-PCR of DNA from a stool sample. The 384 wells used in the experiment are displayed. Those colored blue contained 25 genome equivalents of DNA from normal cells. Each of these registered positive with MB-RED and the RED/GREEN ratios were 1.0+/−0.1 (mean +/−1 standard deviation). The wells colored yellow contained no template DNA and each was negative with MB-RED (i.e., fluorescence <3500 fluorescence units.). The other wells contained diluted DNA from the stool sample. Those registering as positive with MB-RED were colored either red or green, depending on their RED/GREEN ratios. Those registering negative with MB-RED were colored white. PCR products from the indicated wells were used for automated sequence analysis. The sequence of WT c-Ki-Ras in well K1 (SEQ ID NO: 7), and mutant c-Ki-Ras in wells C10, E11, M10, and L12 (SEQ ID NO: 14), and well F21 (SEQ ID NO: 15) were analyzed.

Digital Analysis of DNA from stool. As a more practical example, we analyzed the DNA from stool specimens of colorectal cancer patients. A representative result of such an experiment is illustrated in FIG. 5. From previous analyses of stool specimens from patients whose tumors contained c-Ki-Ras gene mutations, we expected that 1% to 10% of the c-Ki-Ras genes purified from stool would be mutant. We therefore set up a 384 well Digital Amplification experiment. As positive controls, 48 of the wells contained 25 genome equivalents of DNA (defined in Materials and Methods) from normal cells. Another 48 wells served as negative controls (no DNA template added). The other 288 wells contained an appropriate dilution of stool DNA. MB-RED fluorescence indicated that 102 of these 288 experimental wells contained PCR products (mean +/−s.d. of 47,000 +/−18,000 SFU) while the other 186 wells did not (2600+/−1500 SFU). The RED/GREEN ratios of the 102 positive wells suggested that five contained mutant c-Ki-Ras genes, with ratios ranging from 2.1 to 5.1. The other 97 wells exhibited ratios ranging from 0.7 to 1.2, identical to those observed in the positive control wells. To determine the nature of the mutant c-Ki-Ras genes in the five positive wells from stool, the PCR products were directly sequenced. The four wells exhibiting RED/GREEN ratios in excess of 3.0 were completely composed of mutant c-Ki-Ras sequence (FIG. 5). The sequence of three of these PCR products revealed Gly12Ala mutations (GGT to GCT at codon 12), while the sequence of the fourth indicated a silent C to T transition at the third position of codon 13. This transition presumably resulted from a PCR error during the first productive cycle of amplification from a WT template. The well with a ratio of 2.1 contained a ~1:1 mix of WT and Gly12Ala mutant sequences. Thus 3.9% (4/102) of the c-Ki-Ras alleles present in this stool sample contained a Gly12Ala mutation. The mutant alleles in the stool presumably arose from the colorectal cancer of the patient, as direct sequencing of PCR products generated from DNA of the cancer revealed the identical Gly12Ala mutation (not shown).

References

1. Vogelstein & Kinzler, (1998) The Genetic Basis of Human Cancer (MCGraw-Hill, Toronto).
2. Lee et al., (1997) Free Radical Biol Med 22, 1259–69.
3. Ozawa, T. (1997) Physiol Rev 77, 425–64.
4. Sidransky et al., (1991) Science 252, 706–09.
5. Sidransky et al., (1992) Science 256, 102–05.
6. Smith-Ravin et al., (1995) Gut 36, 81–6.
7. Mills et al., (1995) J. Natl Cancer Inst 87, 1056–60.
8. Mao et al. (1994) Cancer Res 54, 1634–37.
9. Brossart et al., (1995) Caner Res 55, 4065–68.
10. Tada et al. (1993) Cancer Res 53, 2472–74.
11. Nawroz et al. (1996) Nature Med 2, 1035–37.
12. Hayashi et al., (1994) Cancer Res 54, 3853–56.
13. Sidransky, (1997) Science 278, 1054–59.
14. Koch et al. (1994) Arch Otolaryngol Head Neck Surg 120, 943–47.
15. Kumar et al., (1990) Science 248, 1101–04.
16. Jonason et al., (1996) Proc Natl Acad Sci USA 93, 14025–29.
17. Ananthaswamy et al. (1999) J Invest Dermatol 112, 763–68.

18. Bar-Eli et al. (1989) Blood 73, 281–83.
19. Collins et al. (1989) Blood 73, 1028–32.
20. Saiki et al. (1986) Nature 324, 163–66.
21. Bos et al. (1987) Nature 327, 293–97.
22. Dicker et al. (1990) Genes Chromosomes Cancer 1, 257–69.
23. Haque et al. (1998) Diagn Mol Pathol 7, 248–52.
24. Haliassos et al. (1989) Nucleic Acids Res 17, 8093–99.
25. Chen et al. (1997) Anal Biochem 244, 191–94.
26. Cha et al. (1992) PCR Methods Appl 2, 14–20.
27. Jiang et al. (1989) Oncogene 4, 923–28.
28. Kahn et al. (1991) Oncogene 6, 1079–83.
29. Kahn et al. (1995) Methods Enzymol 255, 452–64.
30. Laken et al., (1998) Nature Biotechnol 16, 1352–56.
31. Whitcombe et al. (1998) Curr Opin Biotechnol 9, 602–08.
32. Day et al. (1999) Nucleic Acids Res 27, 1820–18.
33. Tyagi et al. (1998) Nature Biotechnol 16, 49–53.
34. Tyagi et al. (1996) Nat Biotechnol 14, 303–08.
35. Lee et al. (1993) Nucleic Acids Res 21, 3761–66.
36. Chiang et al. (1996) Genome Res 6, 1013–26.
37. Heid et al. (1996) Genome Res 6. 986–94.
38. Paris et al. (1998) Nucleic Acids Res 26, 3789–93.
39. Gibson et al. (1997) Clin Chem 43, 1336–41.
40. Chen et al. (1999) Genome Res 9, 492–98.
41. Szollosi et al. (1998) Cytometry 34, 159–79.
42. Cortopassi et al. (1992) Mutat Res 277, 239–49.
43. Monckton et al. (1991) Genomics 11, 465–67.
44. Chou et al. (1992) Nucleic Acids Res 20, 1717–23.
45. Kellogg et al. (1994) Biotechniques 16, 1134–37.
46. Li et al. (1988) Nature 335, 414–17.
47. Schmitt et al. (1994) Forensic Sci Int 66, 129–41.
48. Navidi et al. (1991) Hum Reprod 6, 836–49.
49. Zhang et al. (1992) Proc Natl Acad Sci USA 89, 5847–51.
50. Jeffreys et al. (1995) Electrophoresis 16, 1577–85.
51. Ruano et al. (1990) Proc Natl Acad Sci USA, 6296–300.
52. Sidransky et al. (1992) Nature 355, 846–47.
53. Parsons et al. (1995) Science 268, 738–40.
54. Lizardi et al. (1998) Nature Genet 19, 225–32.
55. Vogelstein (1989) Science 244, 207–11.
56. Marras et al. (1999) Genet Anal 14, 151–56.

What is claimed is:

1. A method for determining the ratio of a selected genetic sequence in a population of genetic sequences, comprising the steps of:

diluting nucleic acid template molecules in a biological sample to form a set comprising a plurality of assay samples;

amplifying the template molecules within the assay samples to form a population of amplified molecules in the assay samples of the set;

analyzing the amplified molecules in the assay samples of the set to determine a first number of assay samples which contain the selected genetic sequence and a second number of assay samples which contain a reference genetic sequence;

comparing the first number to the second number to ascertain a ratio which reflects the composition of the biological sample.

2. The method of claim 1 wherein the step of diluting is performed until at least one-tenth of the assay samples in the set comprise a number (N) of molecules such that 1/N is larger than the ratio of selected genetic sequences to total genetic sequences required for the step of analyzing to determine the presence of the selected genetic sequence.

3. The method of claim 1 wherein the step of diluting is performed until between 0.1 and 0.9 of the assay samples yield an amplification product when subjected to a polymerase chain reaction.

4. The method of claim 1 wherein the step of diluting is performed until all of the assay samples yield an amplification product when subjected to a polymerase chain reaction and each assay sample contains less than 10 nucleic acid template molecules containing the reference genetic sequence.

5. The method of claim 1 wherein the step of diluting is performed until all of the assay samples yield an amplification product when subjected to a polymerase chain reaction and each assay sample contains less than 100 nucleic acid template molecules containing the reference genetic sequence.

6. The method of claim 1 wherein the biological sample is cell-free.

7. The method of claim 1 wherein the number of assay samples within the set is greater than 10.

8. The method of claim 1 wherein the number of assay samples within the set is greater than 50.

9. The method of claim 1 wherein the number of assay samples within the set is greater than 100.

10. The method of claim 1 wherein the number of assay samples within the set is greater than 500.

11. The method of claim 1 wherein the number of assay samples within the set is greater than 1000.

12. The method of claim 1 wherein the step of amplifying and the step of analyzing are performed on assay samples in the same receptacle.

13. The method of claim 1 wherein a molecular beacon probe is used in the step of analyzing, wherein a molecular beacon probe is an oligonucleotide with a stem-loop structure having a photoluminescent dye at one of the 5' or 3' ends and a quenching agent at the opposite 5' or 3' end.

14. The method of claim 1 wherein the step of analyzing employs gel electrophoresis.

15. The method of claim 1 wherein the step of analyzing employs hybridization to at least one nucleic acid probe.

16. The method of claim 1 wherein the step of analyzing employs hybridization to at least two nucleic acid probe.

17. The method of claim 13 wherein two molecular beacon probes are used, each having a different photoluminescent dye.

18. The method of claim 13 wherein the molecular beacon probe detects a wild-type selected genetic sequence better than a mutant selected genetic sequence.

19. The method of claim 1 wherein the step of amplifying employs a single pair of primers.

20. The method of claim 1 wherein the step of amplifying employs a polymerase which is activated only after heating.

21. The method of claim 1 wherein the step of amplifying employs at least 40 cycles of heating and cooling.

22. The method of claim 1 wherein the step of amplifying employs at least 50 cycles of heating and cooling.

23. The method of claim 1 wherein the step of amplifying employs at least 60 cycles of heating and cooling.

24. The method of claim 1 wherein the biological sample is selected from the group consisting of stool, blood, and lymph nodes.

25. The method of claim 1 wherein the biological sample is blood or bone marrow of a leukemia or lymphoma patient who has received anti-cancer therapy.

26. The method of claim 1 wherein the selected genetic sequence is a translocated allele.

27. The method of claim 1 wherein the selected genetic sequence is a wild-type allele.

28. The method of claim 1 wherein the selected genetic sequence is within an amplicon which is amplified during neoplastic development.

29. The method of claim 1 wherein the selected genetic sequence is a rare exon sequence.

30. The method of claim 1 wherein the nucleic acid template molecules comprise cDNA of RNA transcripts and the selected genetic sequence is present on a cDNA of a first transcript and the reference genetic sequence is present on a cDNA of a second transcript.

31. The method of claim 1 wherein the selected genetic sequence comprises a first mutation and the reference genetic sequence comprises a second mutation.

32. The method of claim 1 wherein the selected genetic sequence and the reference genetic sequence are on distinct chromosomes.

33. A molecular beacon probe comprising:
an oligonucleotide with a stem-loop structure having a photoluminescent dye at one of the 5' or 3' ends and a quenching agent at the opposite 5' or 3' end, wherein the loop consists of 16 base pairs, wherein the loop has a $T_m$ of 50–51° C. and the stem consists of 4 base pairs having a sequence 5'-CACG-3'.

34. The probe of claim 33 wherein the molecular beacon probe detects a wild-type selected genetic sequence better than a mutant selected genetic sequence.

35. The probe of claim 33 wherein the molecular beacon probe detects a mutant genetic sequence better than a wild-type genetic sequence.

36. A molecular beacon probe comprising:
an oligonucleotide with a stem-loop structure having a photoluminescent dye at one of the 5' or 3' ends and a quenching agent at the opposite 5' or 3' end, wherein the loop consists of 19–20 base pairs, wherein the loop has a $T_m$ of 54–56° C. and the stem consists of 4 base pairs having a sequence 5'-CACG-3'.

37. A pair of molecular beacon probes comprising:
a first molecular beacon probe which is an oligonucleotide with a stem-loop structure having a first photoluminescent dye at one of the 5' or 3' ends and a quenching agent at the opposite 5' or 3' end, wherein the loop consists of 16 base pairs having a $T_m$ of 50–51° C. and the stem consists of 4 base pairs having a sequence 5'-CACG-3'; and
a second molecular beacon probe which is an oligonucleotide with a stem-loop structure having a second photoluminescent dye at one of the 5' or 3' ends and a quenching agent at the opposite 5' or 3' end, wherein the loop consists of 19–20 base pairs having a $T_m$ of 54–56° C. and the stem consists of 4 base pairs having a sequence 5'-CACG-3';
wherein the first and the second photoluminescent dyes are distinct.

38. A method for determining the ratio of a selected genetic sequence in a population of genetic sequences, comprising the steps of:

amplifying template molecules within a set comprising a plurality of assay samples to form a population of amplified molecules in each of the assay samples of the set;

analyzing the amplified molecules in the assay samples of the set to determine a first number of assay samples which contain the selected genetic sequence and a second number of assay samples which contain a reference genetic sequence, wherein at least one-fiftieth of the assay samples in the set comprise a number (N) of molecules such that 1/N is larger than the ratio of selected genetic sequences to total genetic sequences required to determine the presence of the selected genetic sequence; comparing the first number to the second number to ascertain a ratio which reflects the composition of the biological sample.

39. The method of claim 38 wherein the number of assay samples within the set is greater than 10.

40. The method of claim 38 wherein the number of assay samples within the set is greater than 50.

41. The method of claim 38 wherein the number of assay samples within the set is greater than 100.

42. The method of claim 38 wherein the number of assay samples within the set is greater than 500.

43. The method of claim 38 wherein the number of assay samples within the set is greater than 1000.

44. The method of claim 38 wherein the step of amplifying and the step of analyzing are performed on assay samples in the same receptacle.

45. The method of claim 38 wherein a molecular beacon probe is used in the step of analyzing, wherein a molecular beacon probe is an oligonucleotide with a stem-loop structure having a photoluminescent dye at one of the 5' or 3' ends and a quenching agent at the opposite 5' or 3' end.

46. The method of claim 38 wherein the step of analyzing employs gel electrophoresis.

47. The method of claim 38 wherein the step of analyzing employs hybridization to at least one nucleic acid probe.

48. The method of claim 38 wherein the step of analyzing employs hybridization to at least two nucleic acid probe.

49. The method of claim 45 wherein two molecular beacon probes are used, each having a different photoluminescent dye.

50. The method of claim 45 wherein the molecular beacon probe detects a wild-type selected genetic sequence better than a mutant selected genetic sequence.

51. The method of claim 38 wherein the step of amplifying employs a single pair of primers.

52. The method of claim 38 wherein the step of amplifying employs a polymerase which is activated only after heating.

53. The method of claim 38 wherein the step of amplifying employs at least 40 cycles of heating and cooling.

54. The method of claim 38 wherein the step of amplifying employs at least 50 cycles of heating and cooling.

55. The method of claim 38 wherein the step of amplifying employs at least 60 cycles of heating and cooling.

56. The method of claim 38 wherein the template molecules are obtained from a body sample selected from the group consisting of stool, blood, and lymph nodes.

57. The method of claim 38 wherein the template molecules are obtained from a body sample of a leukemia or lymphoma patient who has received anti-cancer therapy, said body sample being selected from the group consisting of blood and bone marrow.

58. The method of claim 38 wherein the selected genetic sequence is a translocated allele.

59. The method of claim 38 wherein the selected genetic sequence is a wild-type allele.

60. The method of claim 38 wherein the selected genetic sequence is within an amplicon which is amplified during neoplastic development.

61. The method of claim 38 wherein the selected genetic sequence is a rare exon sequence.

62. The method of claim 38 wherein the nucleic acid template molecules comprise cDNA of RNA transcripts and the selected genetic sequence is present on a cDNA of a first transcript and the reference genetic sequence is present on a cDNA of a second transcript.

63. The method of claim 38 wherein the selected genetic sequence comprises a first mutation and the reference genetic sequence comprises a second mutation.

64. The method of claim 38 wherein the selected genetic sequence and the reference genetic sequence are on distinct chromosomes.

* * * * *

(12) EX PARTE REEXAMINATION CERTIFICATE (10360th)

United States Patent
Vogelstein et al.

(10) Number: US 6,440,706 C1
(45) Certificate Issued: Oct. 24, 2014

(54) DIGITAL AMPLIFICATION

(75) Inventors: Bert Vogelstein, Baltimore, MD (US); Kenneth W. Kinzler, BelAir, MD (US)

(73) Assignee: The Johns Hopkins University, Baltimore, MD (US)

Reexamination Request:
No. 90/012,894, Jun. 17, 2013

Reexamination Certificate for:
Patent No.: 6,440,706
Issued: Aug. 27, 2002
Appl. No.: 09/613,826
Filed: Jul. 11, 2000

Related U.S. Application Data

(60) Provisional application No. 60/146,792, filed on Aug. 2, 1999.

(51) Int. Cl.
*C12N 15/09* (2006.01)
*C12Q 1/68* (2006.01)

(52) U.S. Cl.
USPC ......... 435/91.2; 435/7.1; 435/91.1; 435/6.12; 536/22.1; 536/23.1; 536/24.3; 536/24.31; 536/24.32; 536/24.33

(58) Field of Classification Search
None
See application file for complete search history.

(56) References Cited

To view the complete listing of prior art documents cited during the proceeding for Reexamination Control Number 90/012,894, please refer to the USPTO's public Patent Application Information Retrieval (PAIR) system under the Display References tab.

*Primary Examiner* — Bruce Campell

(57) ABSTRACT

The identification of pre-defined mutations expected to be present in a minor fraction of a cell population is important for a variety of basic research and clinical applications. The exponential, analog nature of the polymerase chain reaction is transformed into a linear, digital signal suitable for this purpose. Single molecules can be isolated by dilution and individually amplified; each product is then separately analyzed for the presence of mutations. The process provides a reliable and quantitative measure of the proportion of variant sequences within a DNA sample.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3, 16, 38 and 48 are determined to be patentable as amended.

Claims 2, 4-12, 14-15, 19-32, 39-44, 46, 47 and 51-64, dependent on an amended claim, are determined to be patentable.

Claims 13, 17, 18, 33-37, 45, 49 and 50 were not reexamined.

1. A method for determining the ratio of a selected genetic sequence in a population of genetic sequences, comprising the steps of:
   diluting *isolated* nucleic acid template molecules [in] *isolated from* a biological sample to form a set comprising a plurality of assay samples;
   amplifying the template molecules within the assay samples to form a population of amplified molecules in the assay samples of the set;
   analyzing the amplified molecules in the assay samples of the set to determine a first number of assay samples which contain the selected genetic sequence and a second number of assay samples which contain a reference genetic sequence;
   comparing the first number to the second number to ascertain a ratio which reflects the composition of the biological sample.

3. The method of claim 1 wherein the step of diluting is performed until between 0.1 and 0.9 of the assay samples yield an amplification product *of at least one of the selected and reference genetic sequences* when subjected to a polymerase chain reaction.

16. The method of claim 1 wherein the step of analyzing employs hybridization to at least two nucleic acid [probe] *probes*.

38. A method for determining the ratio of a selected genetic sequence in a population of genetic sequences, comprising the steps of:
   *distributing cell-free nucleic acid template molecules from a biological sample to form a set comprising a plurality of assay samples;*
   amplifying *the nucleic acid* template molecules [within a set comprising a plurality of assay samples] to form a population of amplified molecules in [each of the] *individual* assay samples of the set;
   analyzing the amplified molecules in the assay samples of the set to determine a first number of assay samples which contain the selected genetic sequence and a second number of assay samples which contain a reference genetic sequence, wherein at least one-fiftieth of the assay samples in the set comprise a number (N) of molecules such that 1/N is larger than the ratio of selected genetic sequences to total genetic sequences required to determine the presence of the selected genetic sequence;
   comparing the first number to the second number to ascertain a ratio which reflects the composition of the biological sample.

48. The method of claim 38 wherein the step of analyzing employs hybridization to at least two nucleic acid [probe] *probes*.

* * * * *